United States Patent
Moroshima et al.

(10) Patent No.: US 7,230,126 B2
(45) Date of Patent: Jun. 12, 2007

(54) METHOD FOR OBTAINING OPTICALLY ACTIVE EPOXIDE

(75) Inventors: Tadashi Moroshima, Takasago (JP); Yasuyoshi Ueda, Takasago (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 10/475,122

(22) PCT Filed: May 10, 2002

(86) PCT No.: PCT/JP02/04561

§ 371 (c)(1), (2), (4) Date: Oct. 17, 2003

(87) PCT Pub. No.: WO02/092587

PCT Pub. Date: Nov. 21, 2002

(65) Prior Publication Data

US 2004/0138484 A1 Jul. 15, 2004

(30) Foreign Application Priority Data

May 11, 2001 (JP) ............................. 2001-141564

(51) Int. Cl.
*C07D 301/02* (2006.01)

(52) U.S. Cl. ..................... 549/541; 549/512; 203/36; 203/37; 203/91

(58) Field of Classification Search ................ 549/512, 549/541, 538; 203/36, 37, 91
See application file for complete search history.

(56) References Cited

U.S. PATENT DOCUMENTS 6,107,511 A    8/2000  Ueda et al.

FOREIGN PATENT DOCUMENTS

| GB | 687991 | 2/1953 |
|----|--------|--------|
| GB | 1035866 | 7/1966 |
| GB | 072697 | 6/1967 |
| GB | 1072697 | 6/1967 |
| JP | 53-147010 | 12/1978 |
| JP | 62-201878 | 9/1987 |
| JP | 9-143175 | 6/1997 |
| WO | WO 98/15544 | 4/1998 |

OTHER PUBLICATIONS

Hamaguchi, S. et al 'Preparation and separation of halomethyloxiranes from reaction mixture by distillation' CA 108:221587 (1988).*

Hamaguchi, S., et al., "Preparation and separation of halomethyloxiranes from reaction mixture by distillation," CA 108:221587 (1988).

* cited by examiner

Primary Examiner—Amelia A. Owens
(74) Attorney, Agent, or Firm—Kenyon & Kenyon LLP

(57) ABSTRACT

The present invention provides a method capable of suppressing a decrease in optical purity due to the exposure to heat during distillation of an optically active epoxide to permit an optically active epoxide of high quality to be simply obtained on an industrial scale. In the method, an optically active epoxide is distilled in the presence of a base to suppress a decrease in optical purity.

13 Claims, No Drawings

METHOD FOR OBTAINING OPTICALLY ACTIVE EPOXIDE

RELATED APPLICATIONS

This is a 371 application of PCT/JP02/04561 filed on 10 May 2002, claiming priority to Japanese Application No. 2001-141564 filed on 11 May 2001, the entire content of which is incorporated herein by reference.

TECHNICAL FIELD

The present invention relates to a method for stably obtaining an optically active epoxide. More specifically, the present invention relates to a method for stably obtaining an optically active epoxide by distillation.

BACKGROUND ART

An optically active epoxide which is useful for medical products, agricultural chemicals and synthetic intermediates thereof is known to cause a decrease in optical purity due to heating (Can. J. Chem. (1976), 54, 3364-76 and J. Chem. Soc., Perkin Trans. 1(1983), 3, 595-9, etc). In obtaining an optically active epoxide by distillation, the optical purity is decreased by heating for distillation. Particularly, in production on an industrial scale, the decrease in the optical purity causes significant adverse effects on yield, quality, and the like. Therefore, an obtaining method using a general-purpose distiller or rectifier accompanied with excessive heating is unsuitable for obtaining an optically active epoxide by industrial distillation or rectification, and the obtaining method is limited to thin-film distillation or the like, thereby limiting an improvement in quality of the optically active epoxide. A means for solving this problem has not yet been known.

SUMMARY OF THE INVENTION

In consideration of the above-described actual situation, an object of the present invention is to provide a simple method for preventing a decrease in the optical purity of an optically active epoxide when the optically active epoxide is obtained by distillation in production on an industrial scale.

As a result of intensive studies for solving the problem, the inventors found that a decrease in optical purity of an optically active epoxide can be suppressed by distillation in the presence of a base to obtain an optically active epoxide of high quality, leading to the achievement of the present invention.

The present invention relates to a method for obtaining an optically active epoxide comprising distilling an optically active epoxide in the presence of a base.

In the obtaining method of the present invention, the optically active epoxide is represented by formula (1):

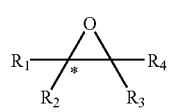
(1)

(wherein $R_1$, $R_2$, $R_3$ and $R_4$ are independently a hydrogen atom, a halogen atom, an alkyl group having 1 to 20 carbon atoms, an alkenyl group having 2 to 20 carbon atoms, an alkynyl group having 2 to 20 carbon atoms, an aryl group having 6 to 20 carbon atoms, an aralkyl group having 7 to 20 carbon atoms, an alkoxy group having 1 to 20 carbon atoms, an aryloxy group having 6 to 20 carbon atoms, an aralkyloxy group having 7 to 20 carbon atoms, an alkoxycarbonyl group having 2 to 20 carbon atoms, an aryloxycarbonyl group having 7 to 20 carbon atoms, an aralkyloxycarbonyl group having 8 to 20 carbon atoms, an acyl group having 1 to 20 carbon atoms, or a cyano group; two of these groups $R_1$, $R_2$, $R_3$ and $R_4$ may be combined to form a ring; $R_1$ and $R_2$ are different groups; and * represents an asymmetric carbon atom).

Furthermore, in the obtaining method of the present invention, $R_1$ is an aryl group, and each of $R_2$, $R_3$ and $R_4$ is a hydrogen atom; an aryl group is a substituted or unsubstituted phenyl group; an aryl group is a phenyl group substituted by 1 to 5 halogen atoms; a halogen atom is a chlorine atom; and an aryl group is a m-chlorophenyl group.

In the obtaining method of the present invention, a nonvolatile base is used as the base; the nonvolatile base is an inorganic base; the inorganic base is at least one of alkali metal carbonates, alkali earth metal carbonates and alkali metal hydrogen carbonates; and the inorganic base is at least one of sodium carbonate, potassium carbonate, sodium hydrogen carbonate and potassium hydrogen carbonate.

In the obtaining method of the present invention, the distillation temperature is 50° C. to 250° C. or 100° C. to 250° C.

DETAILED DESCRIPTION

The present invention will be described in detail below.

A method for obtaining an optically active epoxide of the present invention comprises distilling an optically active epoxide in the presence of a base.

The optically active epoxide used in the present invention is not limited as long as it can be obtained by distillation. More specifically, the optically active epoxide is a compound represented by, for example, formula (1):

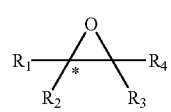
(1)

In formula (1), $R_1$, $R_2$, $R_3$ and $R_4$ are each independently a hydrogen atom, a halogen atom, an alkyl group having 1 to 20 carbon atoms, an alkenyl group having 2 to 20 carbon atoms, an alkynyl group having 2 to 20 carbon atoms, an aryl group having 6 to 20 carbon atoms, an aralkyl group having 7 to 20 carbon atoms, an alkoxy group having 1 to 20 carbon atoms, an aryloxy group having 6 to 20 carbon atoms, an aralkyloxy group having 7 to 20 carbon atoms, an alkoxycarbonyl group having 2 to 20 carbon atoms, an aryloxycarbonyl group having 7 to 20 carbon atoms, an aralkyloxycarbonyl group having 8 to 20 carbon atoms, an acyl group having 1 to 20 carbon atoms, or a cyano group; two of these groups $R_1$, $R_2$, $R_3$ and $R_4$ may be combined to form a ring; $R_1$ and $R_2$ are different groups; and * represents an asymmetric carbon atom.

Each of the groups represented by $R_1$, $R_2$, $R_3$ and $R_4$ will be described below.

Examples of a halogen atom include a chlorine atom, a bromine atom, an iodine atom, and the like. A chlorine atom and bromine atom are preferred.

Although an alkyl group having 1 to 20 carbon atoms is not limited, an alkyl group having 1 to 8 carbon atoms is preferred. Examples of such an alkyl group include a methyl group, an ethyl group, a n-propyl group, an i-propyl group, a n-butyl group, a t-butyl group, a n-pentyl group, a hexyl group, a cyclohexyl group, a heptyl group, an octyl group, and the like.

Although an alkenyl group having 2 to 20 carbon atoms is not limited, an alkenyl group having 2 to 8 carbon atoms is preferred. Examples of such an alkenyl group include a vinyl group, an allyl group, a propenyl group, a butenyl group, a pentenyl group, a cyclopentenyl group, a hexenyl group, a heptenyl group, an octenyl group, and the like.

Although an alkynyl group having 2 to 20 carbon atoms is not limited, an alkynyl group having 2 to 8 carbon atoms is preferred. Examples of such an alkynyl group include an ethynyl group, a propynyl group, a butynyl group, a pentynyl group, a hexynyl group, a heptynyl group, an octynyl group, and the like.

Although an aryl group having 6 to 20 carbon atoms is not limited, an aryl group having 6 to 12 carbon atoms is preferred. Examples of such an aryl group include a phenyl group, a naphthyl group, a p-tolyl group, a xylyl group and the like.

Although an aralkyl group having 7 to 20 carbon atoms is not limited, an aralkyl group having 7 to 15 carbon atoms is preferred. Examples of such an aralkyl group include a benzyl group, a phenethyl group, a phenylpropyl group, a phenylbutyl group, and the like.

Although an alkoxy group having 1 to 20 carbon atoms is not limited, an alkoxy group having 1 to 12 carbon atoms is preferred. Examples of such an alkoxy group include a methoxy group, an ethoxy group, a n-propoxy group, an i-propoxy group, a n-butoxy group, a t-butoxy group, a pentyloxy group, a hexyloxy group, and the like.

Although an aryloxy group having 6 to 20 carbon atoms is not limited, an aryloxy group having 6 to 15 carbon atoms is preferred. Examples of such an aryloxy group include a phenoxy group, a naphthyloxy group, a p-tolyloxy group, a xylyloxy group, and the like.

Although an aralkyloxy group having 7 to 20 carbon atoms is not limited, an aralkyloxy group having 7 to 15 carbon atoms is preferred. Examples of such an aralkyloxy group include a benzyloxy group, a phenethyloxy group, a phenylpropoxy group, a phenylbutoxy group, and the like.

Although an alkoxycarbonyl group having 2 to 20 carbon atoms is not limited, an alkoxycarbonyl group having 2 to 10 carbon atoms is preferred. Examples of such an alkoxycarbonyl group include a methoxycarbonyl group, an ethoxycarbonyl group, an i-propoxycarbonyl group, a t-butoxycarbonyl group, a pentyloxycarbonyl group, a hexyloxycarbonyl group, and the like.

Although an aryloxycarbonyl group having 7 to 20 carbon atoms is not limited, an aryloxycarbonyl group having 7 to 15 carbon atoms is preferred. Examples of such an aryloxycarbonyl group include a phenoxycarbonyl group, a naphthyloxycarbonyl group, a p-tolyloxycarbonyl group, a xylyloxycarbonyl group, and the like.

Although an aralkyloxycarbonyl group having 8 to 20 carbon atoms is not limited, an aralkyloxycarbonyl group having 8 to 15 carbon atoms is preferred. Examples of such an aralkyloxycarbonyl group include a benzyloxycarbonyl group, a phenethyloxycarbonyl group, a phenylpropoxycarbonyl group, a phenylbutoxycarbonyl group, and the like.

Although an acyl group having 1 to 20 carbon atoms is not limited, an acyl group having 1 to 12 carbon atoms is preferred. Examples of such an acyl group include a formyl group, an acetyl group, a propanoyl group, a butyryl group, a valeryl group, a pivaloyl group, a hexanoyl group, a benzoyl group, and the like.

Each of these groups may be further substituted by another atom or substituent.

Examples of other atoms include an oxygen atom, a nitrogen atom, a sulfur atom, and the like. A carbon atom of each group may be substituted by any of these atoms.

Examples of substituents include a hydroxyl group, an alkoxy group having 1 to 6 carbon atoms, an amino group, a halogen atom, and the like. Each of the above-described groups may be substituted by any of these substituents.

Each of the groups represented by $R_1$, $R_2$, $R_3$ and $R_4$ and substituents thereof may be a straight chain, a branched form, a cyclic form or a noncyclic form.

Two groups of $R_1$, $R_2$, $R_3$ and $R_4$ may be combined together to form a ring. Although the formed ring is not limited, for example, 7-oxabicyclo[4.1.0] heptane-2-one, 9-oxabicyclo[6,1,0] none-4-ene, or the like can be formed.

In the optically active epoxide (1), $R_1$ is preferably an aryl group. Preferably, $R_1$ is an aryl group, and at least one of $R_2$, $R_3$ and $R_4$ is a hydrogen atom, and more preferably, $R_1$ is an aryl group, and at least two of $R_2$, $R_3$ and $R_4$ are hydrogen atoms. Most preferably, $R_1$ is an aryl group, and all of $R_2$, $R_3$ and $R_4$ are hydrogen atoms.

Furthermore, an aryl group is preferably a substituted or unsubstituted phenyl group, more preferably a phenyl group substituted by 1 to 5 halogen atoms, and most preferably a phenyl group substituted by a chlorine atom. Particularly, a m-chlorophenyl group is preferred.

As the base used in the present invention, an inorganic base such as an alkali or alkali earth metal carbonate or hydroxide, an alkali metal hydrogen carbonate, or the like, or an organic base such as a tertiary amine, a quaternary ammonium hydroxide, or the like may be used.

Examples of such bases include alkali metal carbonates such as sodium carbonate, potassium carbonate, lithium carbonate, and the like; alkali earth metal carbonates such as calcium carbonate, magnesium carbonate, and the like; alkali metal hydrogen carbonates such as sodium hydrogen carbonate, potassium hydrogen carbonate, lithium hydrogen carbonate, and the like; alkali metal hydroxides such as sodium hydroxide, potassium hydroxide, lithium hydroxide, and the like; alkali earth metal hydroxides such as calcium hydroxide, magnesium hydroxide, and the like; tertiary amines such as triethylamine, tripropylamine, tributylamine, triamylamine, pyridine, N-methylmorpholine, and the like; tetramethyl, tetraethyl, tetrapropyl, tetraamyl and benzyltrimethyl quaternary ammonium hydroxides, and the like. However, the base is not limited to these compounds.

Of these bases, a nonvolatile base is preferred. The term "nonvolatile" means that substantially no distillate occurs under distillation conditions, without an essentially adverse effect on product quality. As the nonvolatile base, for example, the inorganic base and the organic base such as a quaternary ammonium hydroxide are preferred, and the inorganic base is more preferred. As the inorganic base, an alkali metal carbonate, an alkali earth metal carbonate, and an alkali metal hydrogen carbonate are more preferred from the viewpoint of low price, low reactivity with the optically active epoxide and ease of waste water treatment. Particularly, sodium carbonate, potassium carbonate, sodium hydrogen carbonate and potassium hydrogen carbonate are preferred. These bases may be used singly or in combination of at least two compounds.

The amount of the base used is not limited, and the use of a large amount of the base has no problem. However, in consideration of economy and operationality, the amount of the base used is generally 0.1 to 30 percent by weight, preferably 0.1 to 10 percent by weight, more preferably 0.1 to 5 percent by weight, and most preferably 0.1 to 2 percent by weight, based on the amount of the distilled substance.

Generally, these bases may be used without any treatment, but the bases may be mixed with other components according to demand. Examples of other components include water, high molecular polymers, a surfactant, and the like.

Although the system of distillation (including rectification) is not limited, batch-system distillation can be generally performed. The distillation conditions depend upon the boiling point of the optically active epoxide used, the ability of the distiller used, etc., and are not limited. However, the distillation temperature is about 50° C. to 250° C., preferably about 70° C. to 220° C., and more preferably about 100° C. to 200° C. Particularly, the effect of the present invention can be exhibited to the maximum extent in distillation at about 100° C. or more, i.e., about 100° C. to about 250° C., preferably about 100° C. to 220° C., and more preferably about 100° C. to 200° C., which causes a significant decrease in the optical purity of an optically active epoxide.

Although the distillation time is not limited, the distillation time is preferably 1 to 200 hours, and more preferably 1 to 150 hours.

BEST MODE FOR CARRYING OUT THE INVENTION

Although the present invention will be described in detail below with reference to examples, the present invention is not limited to these examples.

EXAMPLE 1

Each of a mixture containing 100 g of m-chlorostyrene oxide (99.3% ee) only was distilled at an internal temperature of 150° C. under a reduced pressure. The optical purity of the resultant m-chlorostyrene oxide was measured. The results are shown in Table 1.

TABLE 1

| Base type | Optical purity of m-chlorostyrene oxide (% ee) |
| --- | --- |
| No addition | 98.4 |
| $Na_2CO_3$ | 99.3 |

REFERENCE EXAMPLE 1

On the assumption of large-scale distillation requiring a long time and significant heating, the experiments below were carried out. 1.4 g each of $Na_2CO_3$, $CaCO_3$, $NaHCO_3$, and $MgCO_3 \cdot Mg(OH)_2$ (combination of two compounds) was added to 70 g of m-chlorostyrene oxide (99.3% ee), and the resultant mixture was heated to 150° C. and stirred. 24 hours after, a change in optical purity of m-chlorostyrene oxide was measured in each of a case in which the base was not added and a case in which the base was added. The results are shown in Table 2. When the base was added, m-chlorostyrene oxide (corresponding to m-chlorostyrene oxide remaining in a reactor in actual distillation) was little racemized after heating. Therefore, it is thought that a target material having high optical purity can be obtained by distillation on a large scale.

TABLE 2

| Base type | Optical purity of m-chlorostyrene oxide (% ee) |
| --- | --- |
| No addition | 95.4 |
| $Na_2CO_3$ | 99.3 |
| $CaCO_3$ | 99.3 |
| $NaHCO_3$ | 99.3 |
| $MgCO_3 \cdot Mg(OH)_2$ | 99.2 |

INDUSTRIAL APPLICABILITY

According to the present invention, an optically active epoxide useful for medical products, agricultural chemicals and synthetic intermediates thereof is distilled in the presence of a base to permit the suppression of a decrease in optical purity and the acquisition of an optically active epoxide of high purity on an industrial scale.

The invention claimed is:

1. A method for obtaining an optically active epoxide comprising distilling an optically active epoxide in the presence of a base in an amount of 0.1 to 30% by weight based on the total amount of the epoxide being distilled.

2. The obtaining method according to claim 1, wherein the optically active epoxide is represented by formula (1):

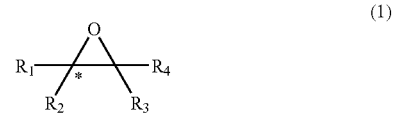

(wherein $R_1$, $R_2$, $R_3$ and $R_4$ are each independently a hydrogen atom, a halogen atom, an alkyl group having 1 to 20 carbon atoms, an alkenyl group having 2 to 20 carbon atoms, an alkynyl group having 2 to 20 carbon atoms, an aryl group having 6 to 20 carbon atoms, an aralkyl group having 7 to 20 carbon atoms, an alkoxy group having 1 to 20 carbon atoms, an aryloxy group having 6 to 20 carbon atoms, an aralkyloxy group having 7 to 20 carbon atoms, an alkoxycarbonyl group having 2 to 20 carbon atoms, an aryloxycarbonyl group having 7 to 20 carbon atoms, an aralkyloxycarbonyl group having 8 to 20 carbon atoms, an acyl group having 1 to 20 carbon atoms, or a cyano group, two of these groups $R_1$, $R_2$, $R_3$ and $R_4$ may be combined together to form a ring, $R_1$ and $R_2$ are different groups, and * represents an asymmetric carbon atom).

3. The obtaining method according to claim 2, wherein $R_1$ is an aryl group, and each of $R_2$, $R_3$ and $R_4$ is a hydrogen atom.

4. The obtaining method according to claim 3, wherein the aryl group is a substituted or unsubstituted phenyl group.

5. The obtaining method according to claim 4, wherein the aryl group is a phenyl group substituted by 1 to 5 halogen atoms.

6. The obtaining method according to claim 5, wherein the halogen atom is a chlorine atom.

7. The obtaining method according to claim 3, wherein the aryl group is a m-chlorophenyl group.

8. The obtaining method according to claim 1, wherein the base is a nonvolatile base.

9. The obtaining method according to claim 8, wherein the nonvolatile base is an inorganic base.

10. The obtaining method according to claim 9, wherein the inorganic base is at least one of alkali metal carbonates, alkali earth metal carbonates, and alkali metal hydrogen carbonates.

11. The obtaining method according to claim 10, wherein the inorganic base is at least one of sodium carbonate, potassium carbonate, sodium hydrogen carbonate, and potassium hydrogen carbonate.

12. The obtaining method according to claim 1, wherein the distillation temperature is 50° C. to 250° C.

13. The obtaining method according to claim 12, wherein the distillation temperature is 100° C. to 250° C.

* * * * *

UNITED STATES PATENT AND TRADEMARK OFFICE
CERTIFICATE OF CORRECTION

PATENT NO. : 7,230,126 B2
APPLICATION NO. : 10/475122
DATED : June 12, 2007
INVENTOR(S) : Moroshima et al.

It is certified that error appears in the above-identified patent and that said Letters Patent is hereby corrected as shown below:

Column 5, line 37-38, "Each of a mixture containing 100g of m-chlorostyrene oxide (99.3% ee) only was distilled" should be changed to --Each of a mixture containing 100g of m-chlorostyrene oxide (99.3% ee) and 2 g of Na2CO3, and 100g of m-chlorostyrene oxide (99.3% ee) only was distilled--.

Signed and Sealed this

Thirtieth Day of September, 2008

JON W. DUDAS
*Director of the United States Patent and Trademark Office*